(12) United States Patent
Kwon et al.

(10) Patent No.: US 8,449,586 B2
(45) Date of Patent: May 28, 2013

(54) METHOD FOR ENHANCING CELL-MEDIATED IMMUNITY

(75) Inventors: Tae-Young Kwon, Seoul (KR); Jeong-Hoon Lim, Seoul (KR)

(73) Assignee: Qray Inc., Gyeonggi-Do (KR)

( * ) Notice: Subject to any disclaimer, the term of this patent is extended or adjusted under 35 U.S.C. 154(b) by 0 days.

(21) Appl. No.: 13/067,994

(22) Filed: Jul. 14, 2011

(65) Prior Publication Data

US 2011/0295342 A1    Dec. 1, 2011

Related U.S. Application Data

(62) Division of application No. 12/292,035, filed on Nov. 10, 2008.

(30) Foreign Application Priority Data

Mar. 4, 2008 (KR) ......................... 10-2008-0020233
Oct. 31, 2008 (KR) ...................... 10-2008-00107471

(51) Int. Cl.
*A61N 5/06* (2006.01)

(52) U.S. Cl.
USPC ............................... 607/88; 607/89; 128/898

(58) Field of Classification Search
USPC ....................... 607/88–94; 128/898
See application file for complete search history.

(56) References Cited

U.S. PATENT DOCUMENTS

| 4,505,545 | A | 3/1985 | Salia-Munoz | 607/90 |
| 5,083,252 | A | 1/1992 | McGuire | 362/293 |
| 5,643,333 | A | 7/1997 | Yun | 607/88 |
| 2007/0129776 | A1 * | 6/2007 | Robins et al. | 607/88 |
| 2007/0219605 | A1 * | 9/2007 | Yaroslavsky et al. | 607/100 |

FOREIGN PATENT DOCUMENTS

GB    2105195    3/1983

OTHER PUBLICATIONS

Takezaki et al., "Light-emitting Diode Phototherapy at 630 +3 nm Increases Local Levels of Skin-homing T-cells in Human Subjects"; J Nippon Med Sch 2006; 73 (2) ; 75-81.
Samoilova et al., "Enhancement of the blood growth promoting activity after exposure of volunteers to visible and infrared polarized light"; Photochem. Photobiol. Sci., 2004, 3, 96-101.
Kubasova et al., "Effect of visible light on some cellular and immune parameters", Immunology and Cell Biology (1995) 73, 239-244.
Mach et al., "T Lymphocytes Induce Endothelial Cell Matrix Metalloproteinase Expression by a CD4OL-Dependent Mechanism"; American Journal of Pathology, vol. 154, No. 1, Jan. 1999, 229-238.
Zhevago et al., "The regulatory effect of polychromatic (visible and infrared) light on human humoral immunity"; Photochem. Photobiol. Sci., 2004, 3, 102-108.

* cited by examiner

*Primary Examiner* — Bill Thompson
*Assistant Examiner* — Jeffrey Lipitz
(74) *Attorney, Agent, or Firm* — Jacobson Holman PLLC

(57) ABSTRACT

Disclosed are a light irradiating device for enhancing cell-mediated immunity and a method using the same. The light irradiating device generates a radiation with a specific peak wavelength at 610±20 nm or 710±30 nm which activates the structure of proteins involved in the activation of T lymphocytes responsible for cell-mediated immunity thus effecting immunopotentiation.

4 Claims, 9 Drawing Sheets

METHOD FOR ENHANCING CELL-MEDIATED IMMUNITY

This is a divisional of application Ser. No. 12/292,035 filed Nov. 10, 2008.

BACKGROUND OF THE INVENTION

1. Field of the Invention

The present invention relates to a light irradiating device for generating radiation from an LED light source, which enhances cell-mediated immunity. Also, the present invention is concerned with a method for enhancing cell-mediated immunity using the same.

2. Description of the Related Art

In humans, immunity, representative of the hallmarks of health, may be greatly weakened by excessive exercise, stress, and other factors.

An improvement in immunity allows the body to more easily surmount stress and to become healthy. In fact, immunopotentiation prevents the body from being infected with pathological microorganisms such as bacteria, fungi, viruses, etc. and, in the case of infection, helps the body overcome diseases and return to the healthy state.

Various studies have been done on the regional or systemic effects of visible light on the body, and thus far, lots of results have been reported concerning neonatal jaundice, improvement of microcirculation, promotion of wound healing, pain relief, control of circadian rhythms, etc.

For this reason, light therapy using visible light has recently become a new trend in natural medicine.

It was not until the late 1980s that light therapy attracted intensive attention thanks to the possibility of being a new alternative medicine. Since then, this medical field has made great progress. It is now widely known that light, whether natural or artificial, has a significant influence on one's usual states of feeling and of mind as well as physical and mental health. For instance, LLLT (low level light therapy) with low-frequency, narrow-band radiation has been proven helpful for pain relief and wound healing.

Studies on the relationship between visible light and immunity may be summarized as follows.

A division of immunity is characterized by the cells involved: humoral immunity is the aspect of immunity that is mediated by B-lymphocytes secreting antibodies such as immunoglobulins whereas the protection provided by cell mediated immunity involves T-lymphocytes acting most significantly.

Visible light has an influence on both of the divisions of immunity.

Irradiation with light in the wavelength range of UV elicits immune reactions mainly at the skin. Because UV light, short in wavelength, cannot penetrate the dermis layer, it mostly acts to suppress cell-mediated immunity at the skin.

On the other hand, visible light ranging in wavelength from 380 to 780 nm penetrates through the epidermis and the dermis to the vessels millimeters distant from the skin surface, so that it can be used to induce photoreactions in blood as well as the irradiated spot.

Samoilova et al. (2004) showed that visible light, unlike UV light, induces blood cells to experience structural and functional changes which are immediately transmitted to entire circulating blood pools through vessels.

Zhevago et al. (2004) reported that exposure to visible light alters immunoglobulin levels in blood with a sharp increase in the levels of IgM and IgA.

According to Kubasova et al. (1995), irradiation with a combination of low-energy density visible light and infrared light was observed to induce the formation of lymphoblasts.

Mach et al. (1999) focused on the effect of visible light on wound healing, reporting that T lymphocytes, responsible for cell-mediated immunity, play an important role in the visible light-induced wound healing.

Based on results from a histological examination on the skin exposed to 630 nm visible light for 8 hours, Takezaki et al. (2006) reported the gathering of T lymphocytes to the exposed skin region.

Visible radiations, although within the same wavelength range, differ from one another in properties depending on wavelength bands. In photodynamic therapy, in fact, visible light is used to potentiate or suppress immunity depending on the wavelengths thereof and the combined use of a sensitizer.

For reference, showing immunosuppressive properties, the UV light UVA or UVB is used for therapy for contact dermatitis or delayed hypersensitivity.

Taken together, results from previous studies indicate that the biological functions of light are determined by its wavelengths and irradiation energies.

Leading to the present, invention, intensive and thorough research into light therapy using visible light, conducted by the present inventors, resulted in the finding that visible light within a specific single wavelength band activates the structure of proteins involved in the activation of T lymphocytes responsible for cell-mediated immunity and that the visible light with the specific wavelength shows far higher immunopotentiation than typical visible light.

The visible light used in the present invention is quite different from the light used in conventional low level light therapy in terms of wavelength band, light coherency and energy density. Whereas the low level light therapy with low-frequency narrow-band light has an influence on the irradiated spot only, the light therapy using the light irradiating device of the present invention enhances cell-mediated immunity which is effected across the whole body.

SUMMARY OF THE INVENTION

It is an object of the present invention to provide a light irradiating device for irradiating and generating light in a specific wavelength band which activates the structure of proteins involved in the activation of T lymphocytes responsible for cell-mediated immunity thus effecting immunopotentiation, and a method for enhancing immunity using the same.

It is another object of the present invention to provide a light irradiating device for generating light in a specific wavelength band, which is so convenient for a user to carry that it can be used amidst daily life activities.

It is a further object of the present invention to provide a light irradiating device for generating light in a specific wavelength band, which can be used as a light source in a backlight unit or is applicable to various goods, such as a display, a cell phone, etc., thus enhancing immunity during the performance of daily life activities.

The above objects can be accomplished by a provision of a light irradiating device irradiating radiations which have a peak wavelength at 610±20 nm or 710±30 nm, radiant power of 0.01~20 mW and a dose ranging in time (T)×light power density (P) from 0.5 mJ·cm$^{-2}$~5 J·cm$^{-2}$, thereby effecting immunopotentiation.

Preferably, the single wavelength of the radiations has a peak at 610±5 nm, 710±5 nm and an radiant power of 0.1~20 mW.

In the light irradiating device, LED, laser diode or OLED may be used as a light source as long as it generates a radiation with a peak wavelength at 610±20 nm or 710±30 nm. In this regard, a band pass filter may be provided for the light source so as to emit the radiation.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Reference now should be made to the drawings to describe the present invention in detail.

Figure 1:
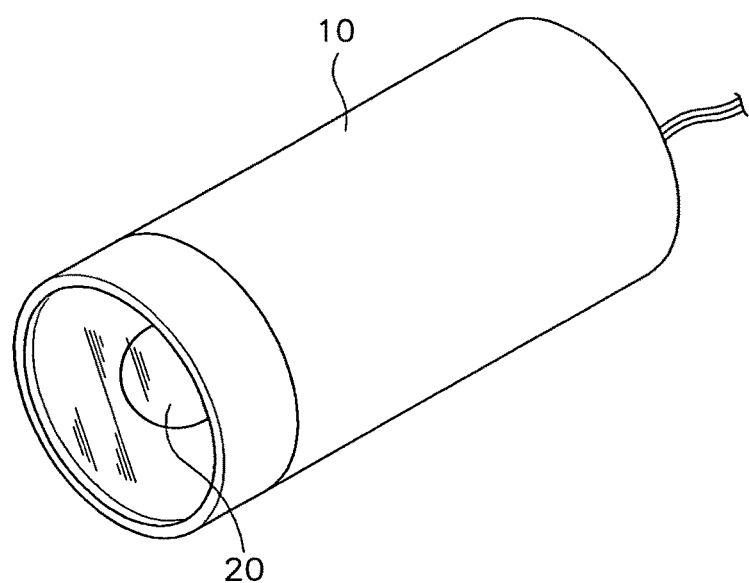
FIG. 1 is an illustration of a light irradiating device in accordance with an embodiment of the present invention.

FIG. 1 is an illustration of a light irradiating device in accordance with an embodiment of the present invention. This light irradiation device comprises a body 10 housing an LED light source 20, designed to irradiate one of single wavelength-band rays with peaks of 610±20 nm and 710±30 nm.

The body 10 may be cylindrical and may be provided at one end thereof with a bandpass filter through which the light generated from the LED 20 passes to have a peak wavelength of 610±20 nm or 710±30 nm.

Figure 2:
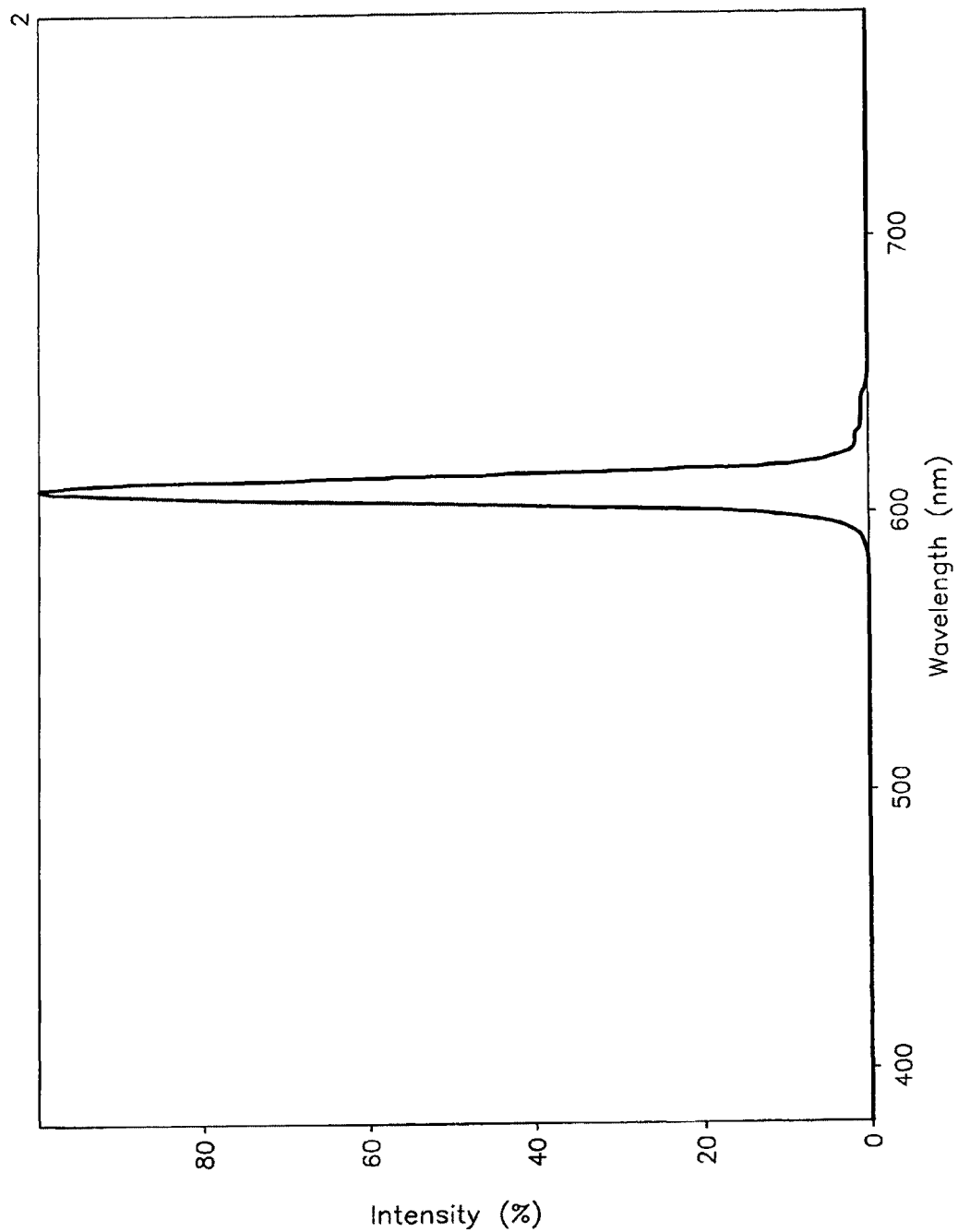
FIG. 2 is a spectrum of light with a wavelength band of 610±20 nm.
Figure 3:
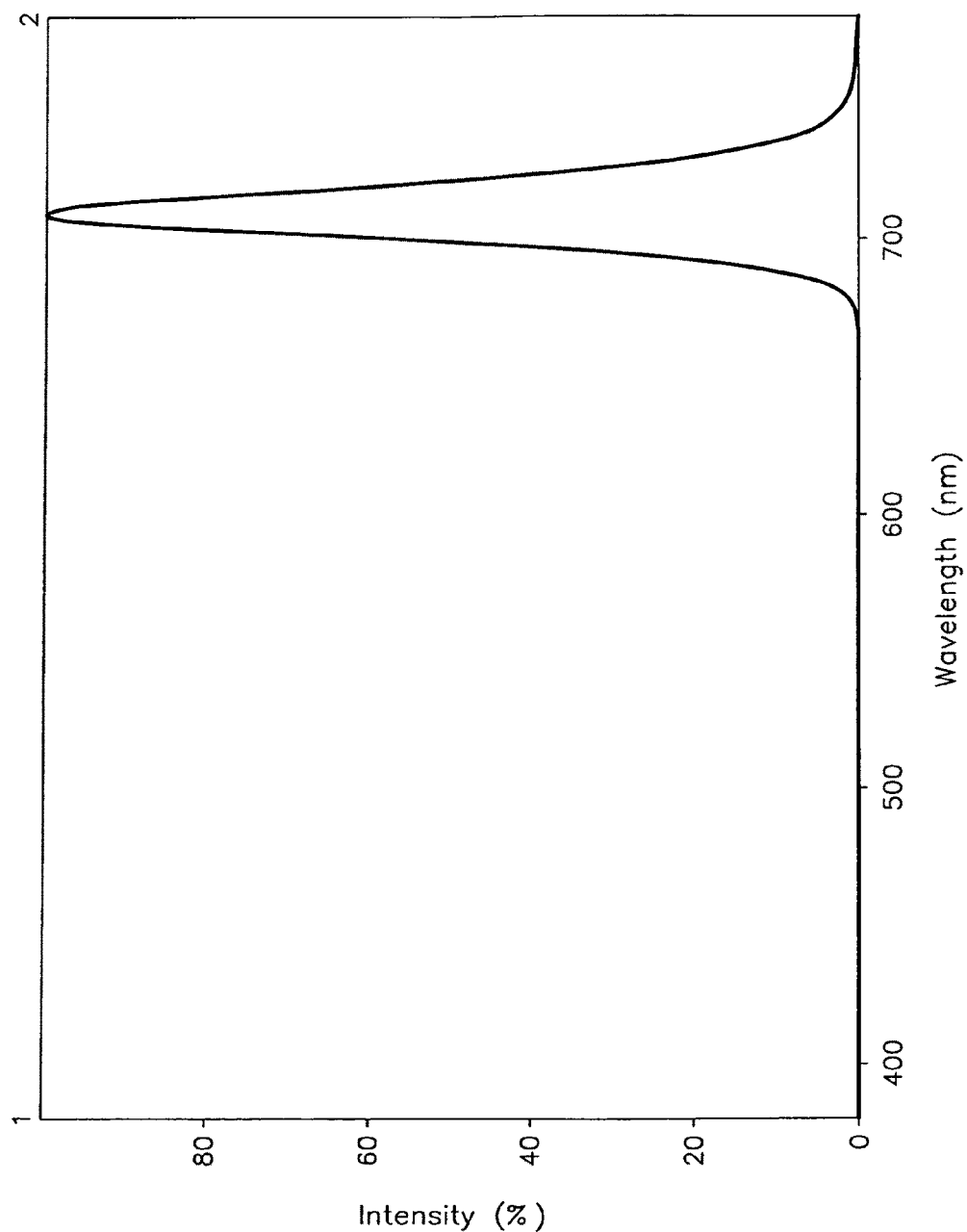
FIG. 3 is a spectrum of light with a wavelength band of 710±30 nm.

With reference to FIGS. 2 and 3, there are spectra of the light irradiated from the light irradiating device of the present invention that are 610±20 nm and 710±30 nm in peak wavelength, respectively.

In accordance with an embodiment of the present invention, the body 10 may be provided with a controller for maintaining the emitted light from the LED 20 at such a wavelength band as to have a peak wavelength of 610±20 nm or 710±30 nm and to be of a predetermined light intensity.

The light emitted from the LED 20 ranges in radiant power from 0.01 to 20 mW.

An experimental result obtained in the development of the present invention indicates that when the light energy of the light emitted from the light irradiating device falls within the range $0.5\ \text{mJ·cm}^{-2} < T \times P < 5\ \text{J·cm}^{-2}$ wherein T is time of single radiation dose and P is light power density, desirable immunopotentiation is obtained.

In order for the light irradiating device of the present invention to have an influence on the immune system, an exposure time of at least 10 μs is required when the emitted light has a light radiant power of 0.01~20 mW and a light power density of $5\ \mu\text{W·cm}^{-2}$~$5\ \text{kW·cm}^{-2}$.

The light irradiating device of the present invention was examined for effects on immunity through the following experiments conducted by the present inventors.

A better understanding of the present invention may be obtained through the following examples which are set forth to illustrate, but are not to be construed as limiting the present invention.

[Animals and Animal Handling]

35 male, specific pathogen-free Sprague-Dawley rats in their $8^{th}$ week of life were bred in a controlled room at 22° C. with a 12-hour light/dark cycle by turning on and off fluorescent lamps and allowed to freely approach water and feedstuff. The experimental animals were handled at the Institute of Biomedical Science and Technology in Konkuk University, Korea, and the experimental protocols were approved by the Institutional Animal Care and Use Committee of Konkuk University.

[Light Irradiating Devices Used in Experiments]

Used were Device A for irradiating light with a peak wavelength of 540 nm, Device B for irradiating light with a peak wavelength of 610 nm, and Device C for irradiating light with a peak wavelength of 710 nm.

Three of the devices were fabricated directly by the present inventors and employed LED light sources and irradiated light with a radiant power of 0.047 mW.

[Irradiation]

The experimental rates were divided into four groups: five exposed to the 540 nm light from Device A; eleven exposed to the 610 nm light from Device B; eleven exposed to 710 nm light from Device C; and eight as a non-exposed control.

While eight control rats were under the fluorescent lamps of the breeding room during the 12 hour light cycle, the experimental groups were irradiated with the light of 540 nm, 610 nm and 710 nm wavelengths from Devices A, B and C, respectively for the same time period.

This procedure was continuously repeated for 28 days.

EXPERIMENTAL EXAMPLE 1

RT-PCR

Total RNA was isolated from 1 ml of whole blood sampled from tail veins of the experimental rats using QiaAmp RNA blood mini (Qiagen GmbH, Hilden, Germany) according to the instructions of the manufacturer.

2 μg of mRNA was used for reverse transcription with Superscript II (Invitrogen, Branfort, Conn., USA). 2 μl of the cDNA thus obtained was amplified by PCR.

PCR primers for IL-1β, IL-4, IL-6 and IFNγ are listed in Table 1, below.

TABLE 1

| Target genes | Directions | Sequences | Product sizes (bp) |
| --- | --- | --- | --- |
| IL-1β | Sense | 5'-CTGTCCTGATGAGAGCATCC-3' | 330 |
|  | Reverse | 5'-TGTCCATTGAGGTGGAGAGC-3' |  |
| IFNγ | Sense | 5'-GCTGTTACTGCCAAGGCACA-3' | 400 |
|  | Reverse | 5'-CGACTCCTTTTCCGCTTCCT-3' |  |
| IL-4 | Sense | 5'-GAGCTATTGATGGGTCTCAGC-3' | 400 |
|  | Reverse | 5'-GGCTTTCCAGGAAGTCTTTCA-3' |  |
| IL-6 | Sense | 5'-ACAAGTCCGGAGAGGAGACT-3' | 490 |
|  | Reverse | 5'-GGATGGTCTTGGTCCTTAGC-3' |  |

After initiation with denaturing at 94° C. for 2 min, PCR was performed with 30 cycles of denaturing at 94° C. for 20 sec, annealing at 58° C. for 40 sec and extension at 72° C. for 1 min.

The PCR products thus obtained were identified by separation on 1% agarose gel.

EXPERIMENTAL EXAMPLE 2

Flow Cytometry

From 1.5 ml of blood samples from the rats, monocytes were isolated with the aid of Ficoll-paque (Amersham Bioscience, Uppsala, Sweden).

Cells were placed at a density of $5 \times 10^5$ cells per test tube into test tubes and treated on ice for 1 hour with 0.25 μg of a PE-conjugated anti-rat-CD4 antibody (BD Bioscience Pharmigen, Cambridge, U.K) or a PE-conjugated anti-rat-CD8a antibody (BD Bioscience Pharmigen, Cambridge, U.K), followed by washing twice with phosphate buffered saline (PBS) and 5% fetal bovine serum.

The cells were measured for fluorescence using a flow cytometer (FACS Calibur, Beckton-Dickinson, Mountain View, Calif., USA) and analyzed using a cell Quest Pro program (Beckton-Dickinson, Mountain View, Calif., USA).

[Results of RT-PCR for Cytokines]

Figure 4:
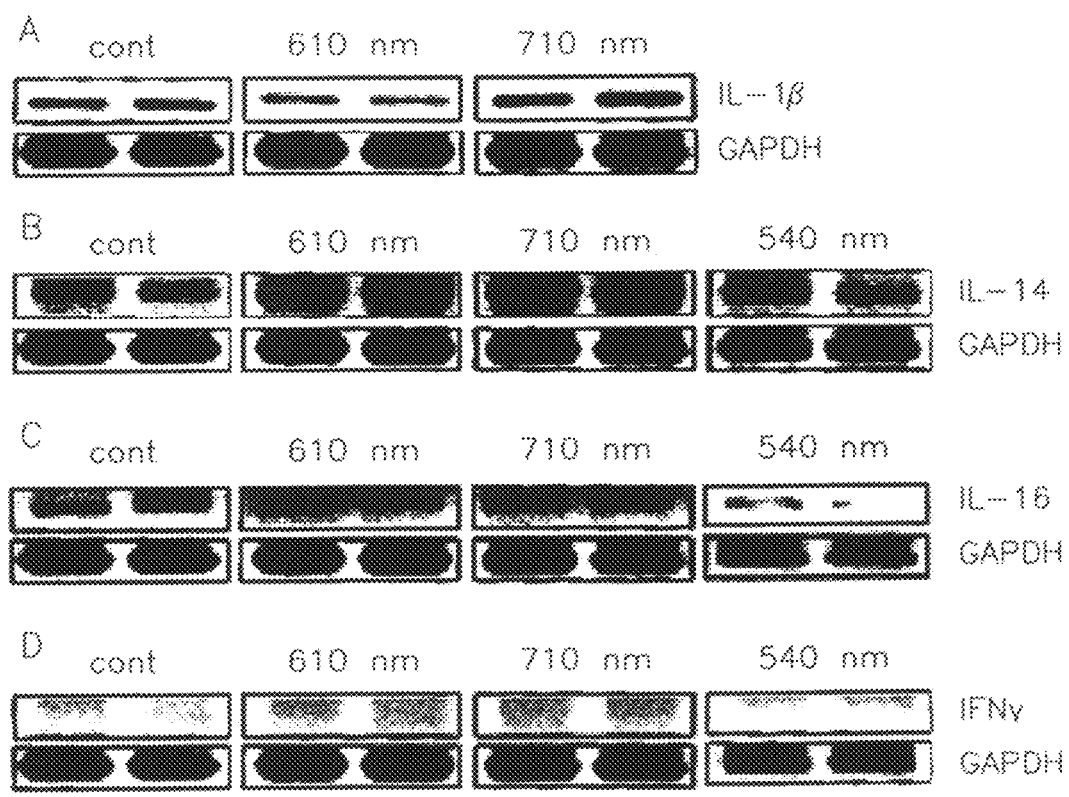
FIG. 4 is a view showing agarose gels on which PCR products from light-exposed or non-exposed rats are separated and stained with ethidium bromide.

With reference to FIG. 4, PCR products obtained in Experimental Example 1 are visualized with ethidium bromide on agarose gel.

As seen in this figure, the experimental groups exposed to 610 nm or 710 nm light were found to increase in IL-4 mRNA level in comparison with the control, but not detected for IFNγ.

An increase in the mRNA level of IL-1β and IL-6 was observed from the 710 nm Group, but with no statistical significance.

No differences were found between the 540 nm Group and the control with regard to the expression levels of IL-4, IL-6 and IFNγ.

Thus, flow cytometry analysis was conducted only on the 610 nm Group, the 710 nm Group and the control as follows.

[Results of Flow Cytometry Analysis for CD4+/CD8+ T Lymphocytes]

Figure 5:
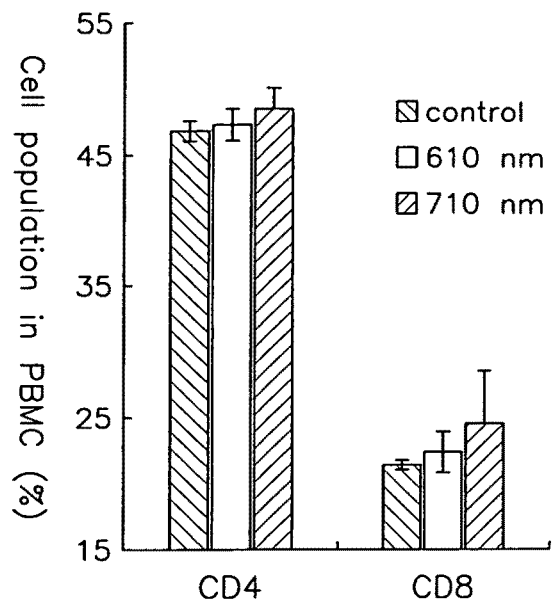
FIG. 5 is a graph showing FACS results of CD4+ T lymphocytes and CD8+ T lymphocytes before exposure to the light.
Figure 6:
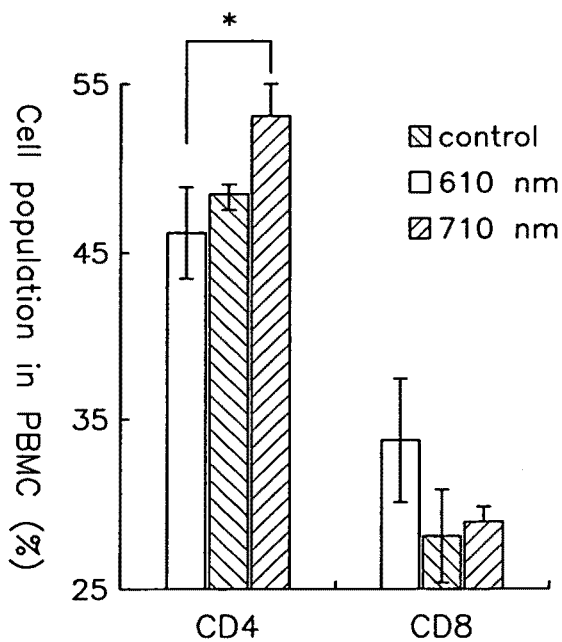
FIG. 6 is a graph showing FACS results of CD4+ T lymphocytes and CD8+ T lymphocytes after-exposure to the light.

Along with the control, the 610 nm Group and the 710 nm Group were analyzed for the distribution of CD4+ and CD8+ T lymphocytes using FACS. % distribution of CD4+ T lymphocytes in the 710 nm Group was increased with a statistical significance ($p<0.05$)), but neither the control nor the 610 nm Group was observed to increase in the % distribution (see FIGS. 5 and 6).

In FIGS. 5 and 6, the difference between the experimental groups was obtained using the one-way ANOVA and the bonferroni procedure.

Significant difference for the distribution of CD8+ was detected in none of the groups.

Figure 7:
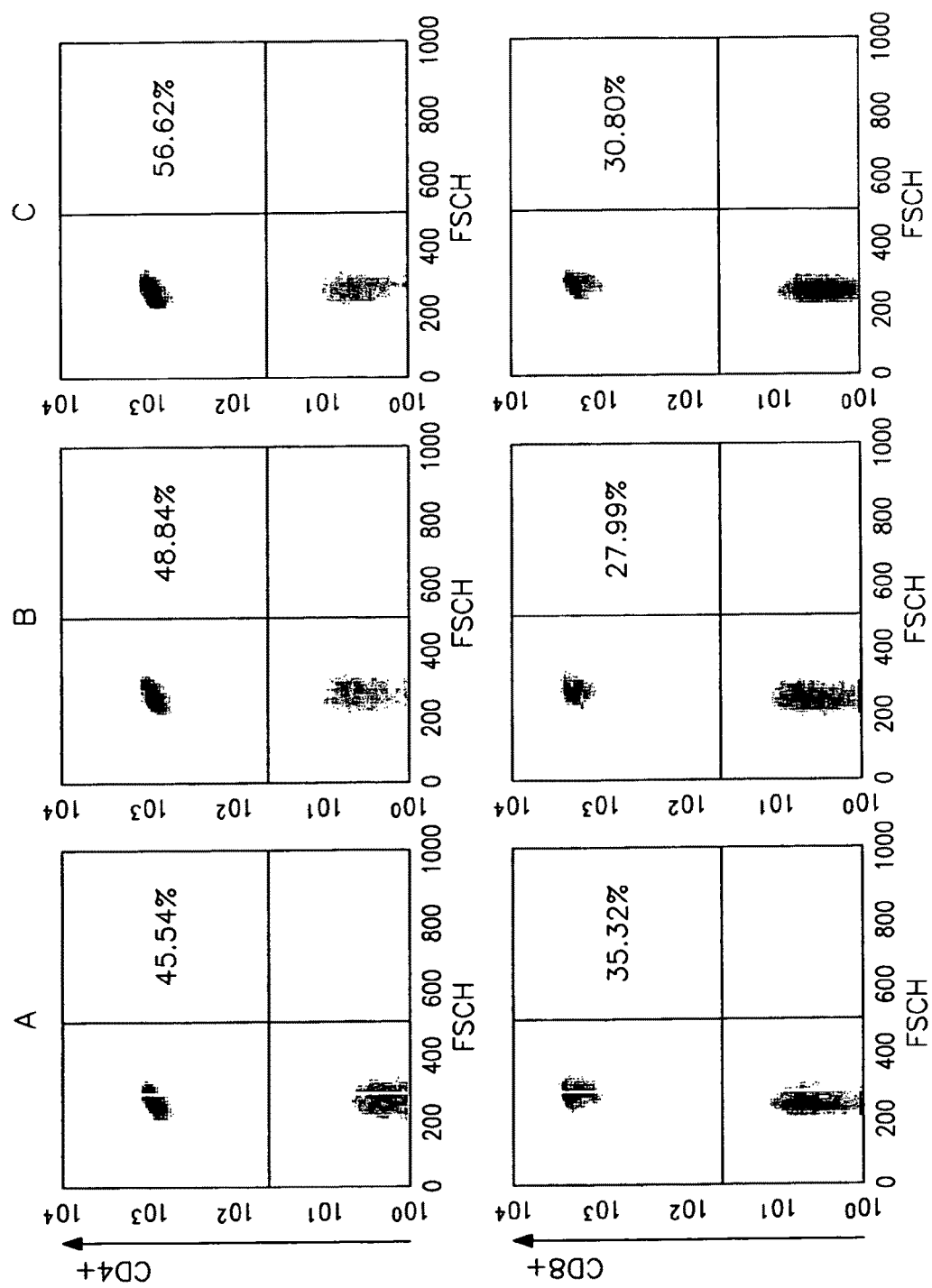
FIG. 7 shows representative flow cytometry of the experimental groups after exposure to the light.

FIG. 7 shows representative flow cytometry of the experimental groups after exposure to the light.

Figure 8:
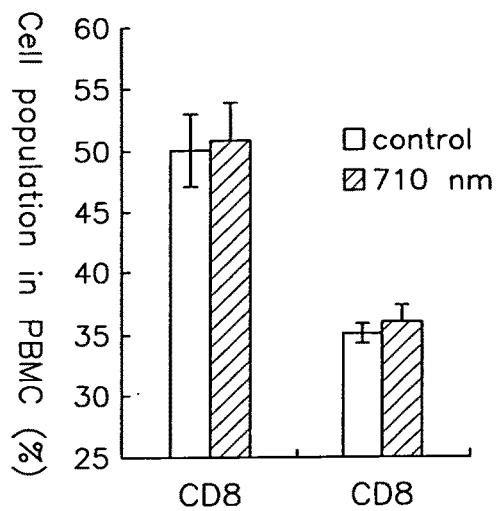
FIG. 8 is a graph showing FACS results of CD4+ T lymphocytes and CD8+ T lymphocytes after the experimental group is exposed to the light and then not exposed for 5 weeks.
Figure 9:
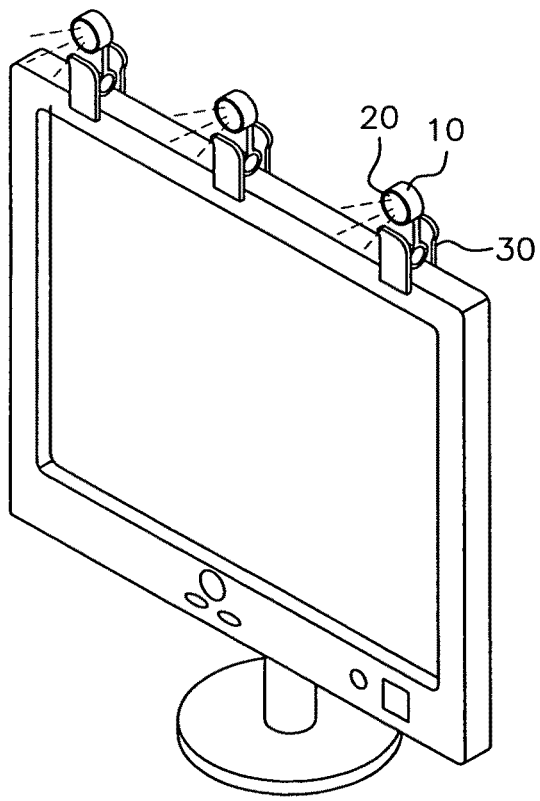
FIG. 9 is an illustrative view showing the application of the light irradiating device to a display monitor.
Figure 10:
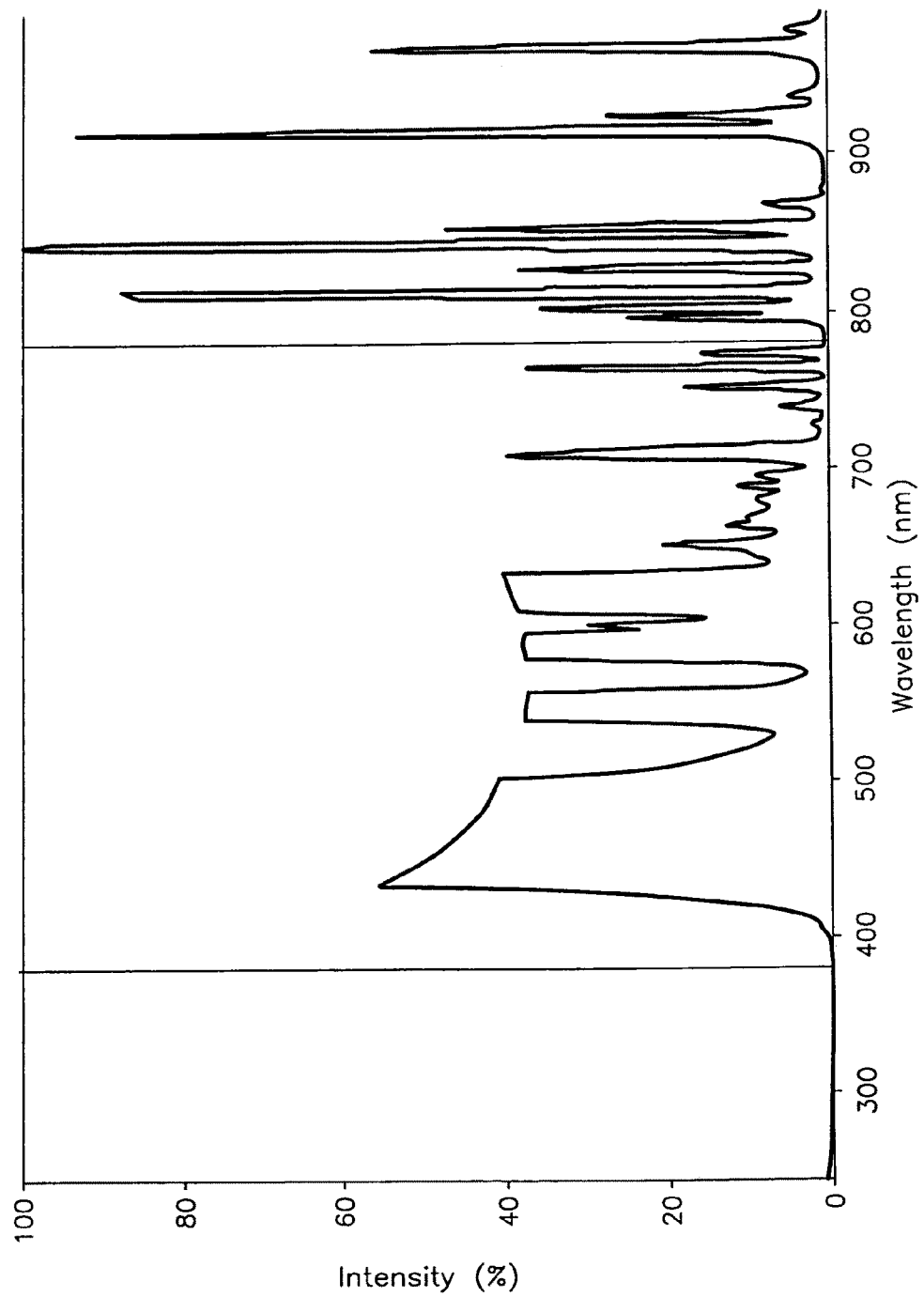
FIG. 10 is spectra of radiation emitted from a typical LCD monitor.
Figure 11:
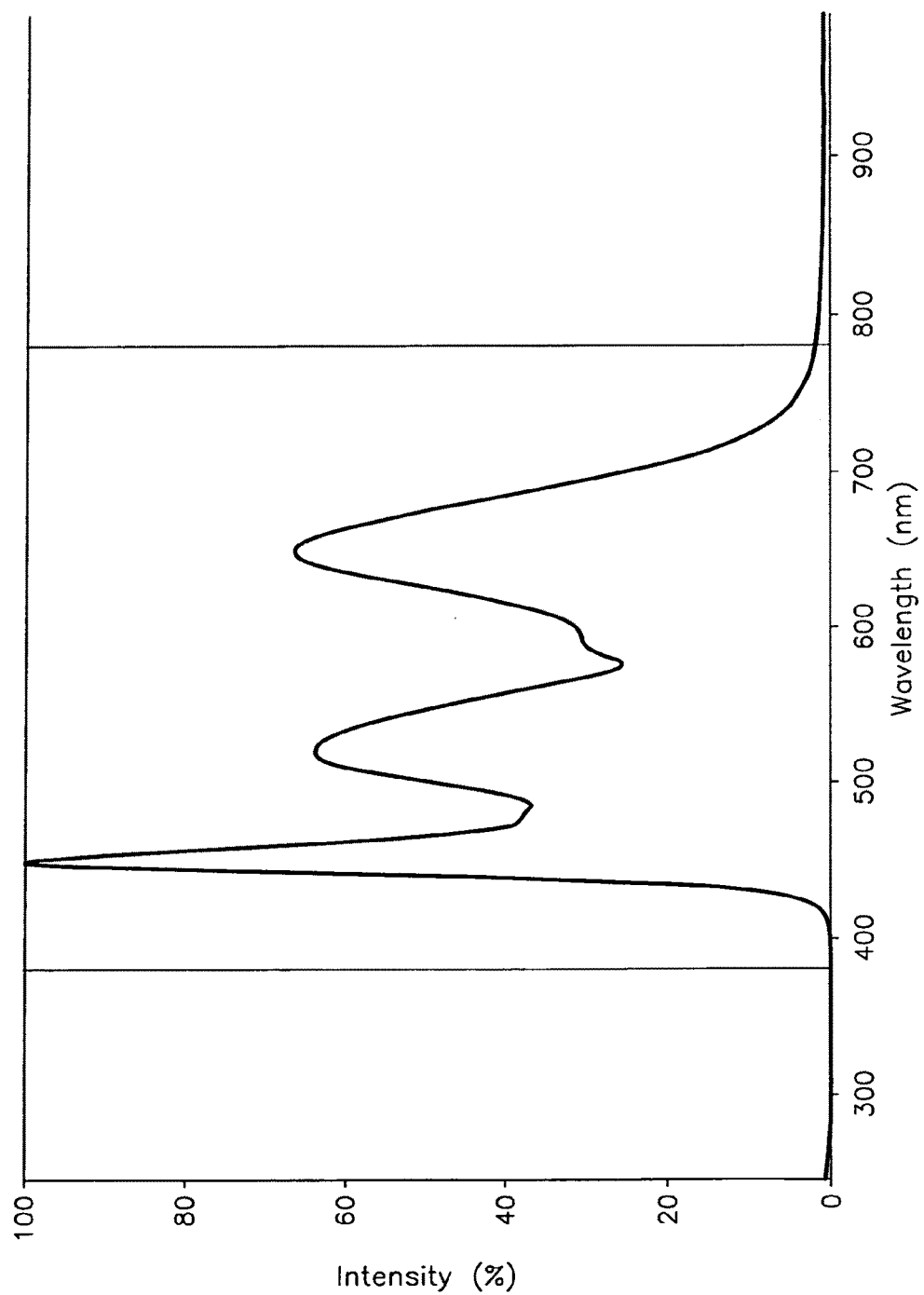
FIG. 11 is spectra of radiation emitted from a typical cell phone.

When, after exposure to the light for four weeks (28 days), the 710 nm Group was not irradiated with the light for five weeks, as in the control, the light-induced CD4+ T lymphocyte increase was not detected, but the level was returned back to the control (see FIG. 8).

The results from the flow cytometric analysis indicate that light with a peak wavelength of 710 nm induced the proliferation of CD4+ helper T lymphocytes.

Also, the results from the RT-PCR analysis show that the LED radiation with a peak wavelength of 710 nm increases the level of IL-4 mRNA, which is produced mainly in CD4+ helper T lymphocytes, supporting the results of the flow cytometry.

In spite of its effective ability to proliferate CD4+ T lymphocytes, the LED radiation with a peak wavelength of 710 nm was found to have no influence on the synthesis of the cytokines IL-1β and IL-6, which are potential inducers of acute phase reactant proteins acting as inflammation indices.

Also, the LED radiation with a peak wavelength of 610 nm was found to activate CD4+ helper T cells by increasing IL-4 mRNA levels, as analyzed on DNA level by RT-PCR.

Accordingly, it is expected that, when illuminated on the body, radiations with peaks at 610 nm±20 nm and at 710±30 nm are useful in immunopoentiation and that the light irradiating device of the present invention may be installed in various goods.

For example, when used as a light source for indoor lamps of rooms and vehicles, for instrument panels of vehicles, etc., the light irradiating device of the present invention is expected to irradiate the body with radiations which are highly effective in immunopotentiation without interference with daily life activities.

When equipped with a mounting means 30, the light irradiating device of the present invention finds a further broad range of applications including neighboring structures (computer monitors, electronic appliances, desks, etc.).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for enhancing immunity, comprising exposing a body to a light irradiating device to activate CD4+ T-lymphocytes responsible for cell-mediated immunity, said light irradiating device comprising a body housing an LED light source which irradiates a radiation with a peak wavelength at 710 nm.

2. The method according to claim 1, wherein the exposing is conducted for at least 10 μs.

3. The method according to claim 1, wherein the radiation emitted from the light irradiating device has an radiant power of 0.01~20 mW.

4. The method according to claim 1, wherein the radiation emitted from the light irradiating device has a radiation dose ranging in time (T)×light power density (P) from $0.5 mJcm^{-2}$ ~ $5 Jcm^{-2}$.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthesized

<400> SEQUENCE: 1
ctgtcctgat gagagcatcc                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthesized

<400> SEQUENCE: 2
tgtccattga ggtggagagc                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthesized

<400> SEQUENCE: 3
gctgttactg ccaaggcaca                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthesized

<400> SEQUENCE: 4
cgactccttt tccgcttcct                                                    20

<210> SEQ ID NO 5
<211> LENGTH: 21
<212> TYPE: DNA
<213> ORGANISM: Artificial Seqence
<220> FEATURE:
<223> OTHER INFORMATION: Synthesized

<400> SEQUENCE: 5
gagctattga tgggtctcag c                                                  21

<210> SEQ ID NO 6
<211> LENGTH: 21
<212> TYPE: DNA
<213> ORGANISM: Artificial Sequence
<220> FEATURE:
<223> OTHER INFORMATION: Synthesized

<400> SEQUENCE: 6
ggctttccag gaagtctttc a                                                  21

<210> SEQ ID NO 7
<211> LENGTH: 20
<212> TYPE: DNA

```
<213> ORGANISM: Artificial Seqence
<220> FEATURE:
<223> OTHER INFORMATION: Synthesized

<400> SEQUENCE: 7
acaagtccgg agaggagact                                              20

<210> SEQ ID NO 8
<211> LENGTH: 20
<212> TYPE: DNA
<213> ORGANISM: Artificial Seqence
<220> FEATURE:
<223> OTHER INFORMATION: Synthesized

<400> SEQUENCE: 8
ggatggtctt ggtccttagc                                              20
```